United States Patent [19]

Hausler et al.

[11] 4,454,006

[45] Jun. 12, 1984

[54] METHOD AND APPARATUS FOR MEASURING TOTAL CORROSION RATE

[75] Inventors: Rudolf H. Hausler, DesPeres; Allen L. Savage, St. Louis, both of Mo.; Jack B. Harrell, Jr., Friendswood, Tex.

[73] Assignee: Petrolite Corporation, St. Louis, Mo.

[21] Appl. No.: 401,165

[22] Filed: Jul. 23, 1982

[51] Int. Cl.³ ............................................. G01N 27/46
[52] U.S. Cl. .................................. 204/1 T; 204/404; 324/65 CR
[58] Field of Search ................... 204/1 C, 404; 73/86; 324/65 CR

[56] References Cited

U.S. PATENT DOCUMENTS

| | | | |
|---|---|---|---|
| 3,406,101 | 10/1968 | Kilpatrick | 204/1 C |
| 3,418,848 | 12/1968 | Schaschl | 73/86 |
| 3,486,996 | 12/1969 | Annand | 204/404 |
| 3,631,338 | 6/1969 | Fitzpatrick et al. | 324/71 R |
| 3,639,876 | 2/1972 | Wilson | 338/13 |
| 4,147,596 | 4/1979 | Baboian et al. | 204/1 T |

Primary Examiner—Aaron Weisstuch
Attorney, Agent, or Firm—Pravel, Gambrell, Hewitt, Kirk & Kimball

[57] ABSTRACT

The corrosion of galvanically coupled metals can be measured and monitored by linear polarization techniques using a test galvanic electrode comprising two individual electrodes of different metals preferably connected end to end with a rigid metallic fastener. The galvanic electrode is treated as a single electrode and can be used as the test electrode in any two or three electrode configuration which includes at least the test electrode and a reference electrode. A three electrode configuration, including also an auxiliary electrode, is adapted for use in combination with the PAIR meter.

5 Claims, 4 Drawing Figures

ANALYSIS OF CURRENT-POTENTIAL RELATIONSHIPS FOR GALVANIC COUPLES $E_1$ — REST POTENTIAL FOR NOBLE ELEMENT
$E_2$ — CORROSION POTENTIAL FOR ACTIVE ELEMENT
$I^1_{corr}$ — CORROSION CURRENT FOR ACTIVE ELEMENT UNCOUPLED
$I^2_{corr}$ — CORROSION CURRENT FOR ACTIVE ELEMENT COUPLED

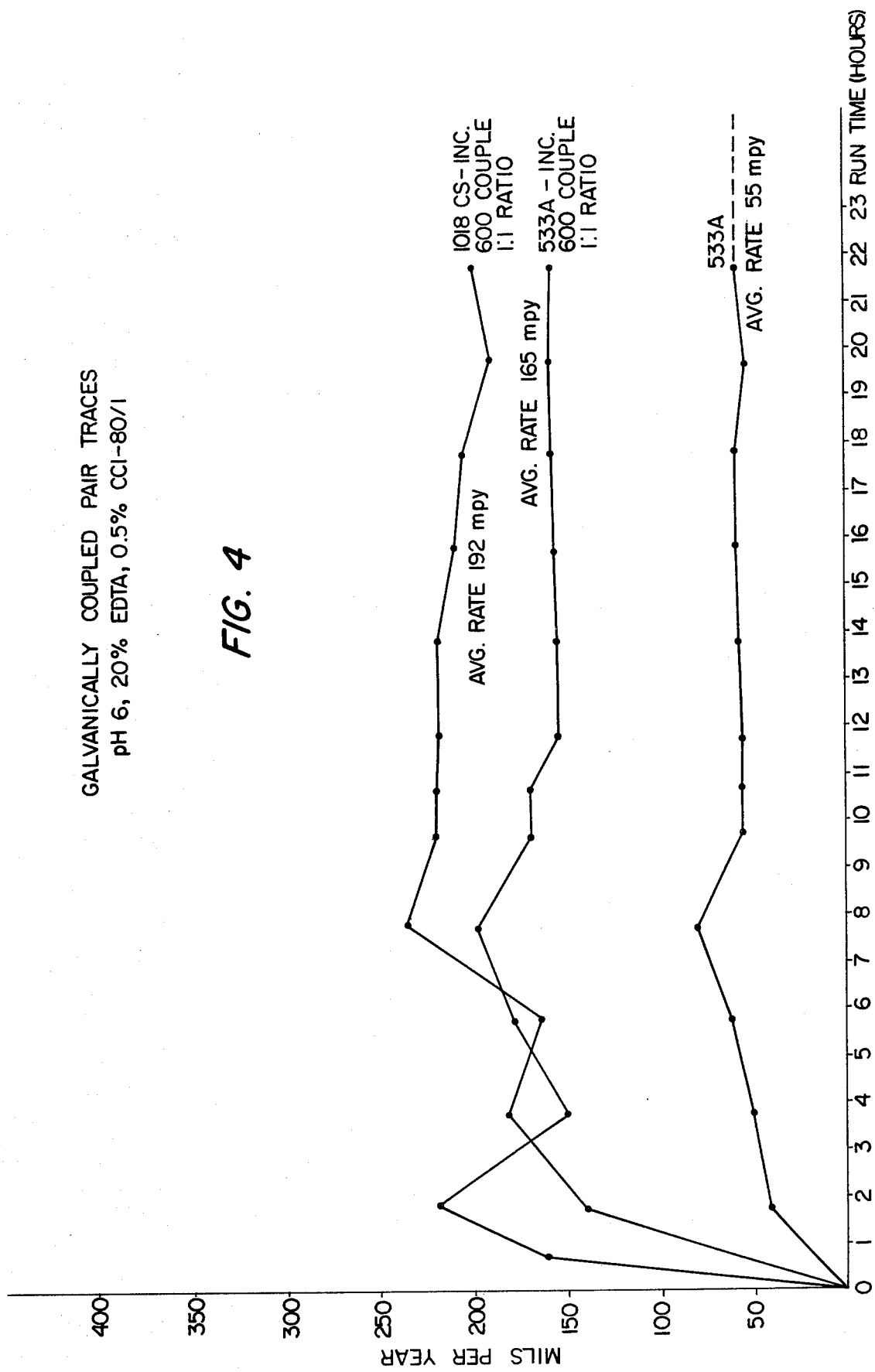

METHOD AND APPARATUS FOR MEASURING TOTAL CORROSION RATE

BACKGROUND AND OBJECTS OF THE INVENTION

This invention relates to measuring corrosion rates and it relates more particularly to instruments and electro-chemical techniques used in the study of corrosion processes, and most particularly to the measurement of the total corrosion rate of a metal subjected to a galvanic current.

Galvanic coupling of metals is unavoidable and must be taken into account in monitoring the corrosion of metals in a great variety of equipment and industrial plants. It had been assumed in the past that the determination of galvanic currents had to be done on two separate isolated electrodes via an ammeter, preferably a zero resistance ammeter. With this method, however, one only measures the acceleration of corrosion due to the galvanic influence but not the actual corrosion rate of the metal in question, since the latter per definition occurs without current in any external circuit. This is a distinct drawback, since galvanic action may, and in many cases does, cause a shift of the corrosion potential of the metal in the anodic (positive) direction. This, in turn, can cause a breakdown of an inhibitor (desorption) causing the metal to corrode much more heavily, an effect which would not necessarily be detected with the zero resistance ammeter.

It is an object of this invention to provide a method for determining the total corrosion rate of a metal subjected to a galvanic current.

It is a further object of this invention to provide a test electrode for use in measuring such total corrosion rate.

It is still an additional object of this invention to provide a probe including such a test electrode for use in measuring such total corrosion rate.

Other objects of the invention will become apparent from the following description.

SUMMARY OF THE INVENTION

The above and other objects of the invention are accomplished by providing a galvanically coupled test electrode comprising two metallic structures differing from each other in composition, and electrically connected to each other by conductive means; and means for attaching such structures to holding means so that a substantial portion of the surfaces of the structures remains exposed. Preferably, the metallic structures are dimensionally substantially identical and their exposed surface areas are substantially identical. In a preferred embodiment, the metallic structures are rod-shaped, e.g., cylindrical, and arranged end to end, with the conductive means connecting them serving also to hold them in such end to end position. The other end of one of the structures is adapted to be rigidly connected to the holding means. Fluid tight sealing means are positioned between the structures and at the opposite ends of the electrode.

The invention also includes a probe for use in measuring galvanic corrosion rate. Such probe comprises the above described preferred embodiment of the galvanically coupled test electrode and at least one additional rod-shaped electrode, the electrodes being substantially dimensionally identical. The electrodes are preferably held by holding means parallel to and in proximity with each other and extending outwardly from the holding means, with fluidtight sealing means being provided between each of the electrodes and the holding means. The holding means is also provided with electrical terminal means and internally disposed conductive means for electrically connecting each electrode to a respective terminal.

In the most preferred embodiment, three electrodes are employed, i.e., the galvanically coupled test electrode, a reference electrode and an auxiliary electrode.

The invention further includes a process for rapidly determining the total rate of corrosion of a galvanic couple of two different metals in a corrosive fluid. This is accomplished by immersing in said solution a galvanically coupled test electrode and a second electrode serving as a reference electrode. The test electrode is polarized a small predetermined amount with respect to the reference electrode and the resultant current measured.

In a preferred embodiment, three electrodes, i.e., the test electrode, the reference electrode and an auxiliary electrode are employed, all being dimensionally substantially identical, having a predetermined exposed surface area and held in fixed proximity to each other. A measurable amount of direct current is passed through a circuit including the test electrode, the fluid and the auxiliary circuit in an amount sufficient to effect a predetermined measurable polarization of the test electrode with respect to the reference electrode.

The measured current, which is representative of the rate of corrosion of the test electrode may be correlated with a corrosion rate polarization resistance ($\Delta E/\Delta I$) curve to determine the corrosion rate. This current may also be measured by an instrument calibrated directly in corrosion rates.

DESCRIPTION OF THE DRAWINGS

FIG. 4 graphically depicts the results obtained in an experiment carried out using electrodes of the type shown in FIG. 2.

DETAILED DESCRIPTION OF THE INVENTION

This invention is based on our finding, theoretically and experimentally, that accelerated corrosion due to galvanic effects can be measured by linear polarization techniques. Linear polarization is the commonly accepted term for corrosion measurements whereby the test electrode is polarized a small measurable amount, for instance, 10 millivolts, with respect to a reference electrode. The resultant current is related to the corrosion rate on the basis of well-established theory. In three electrode instruments such as the PAIR instrument, a dedicated reference electrode is used, while in two electrode instruments the auxiliary electrode is also used as reference electrode. While the use of a PAIR instrument is preferred, the present invention is applicable to any instrument based on the linear polarization technique subject to the limitations of these techniques. The application of linear polarization to the measurement of galvanically accelerated corrosion also provides the advantage of measuring the total corrosion rate of the metal rather than only the acceleration due to the galvanic coupling.

The PAIR instrument referred to above and the technique employed in conjunction therewith are described and claimed in U.S. Pat. No. 3,406,101, issued Oct. 15, 1968 to James M. Kilpatrick, the disclosure of which is hereby incorporated by reference. Probes and instruments for carrying out the PAIR technique are available from the Petreco Division of the Petrolite Corporation.

Figure 1:
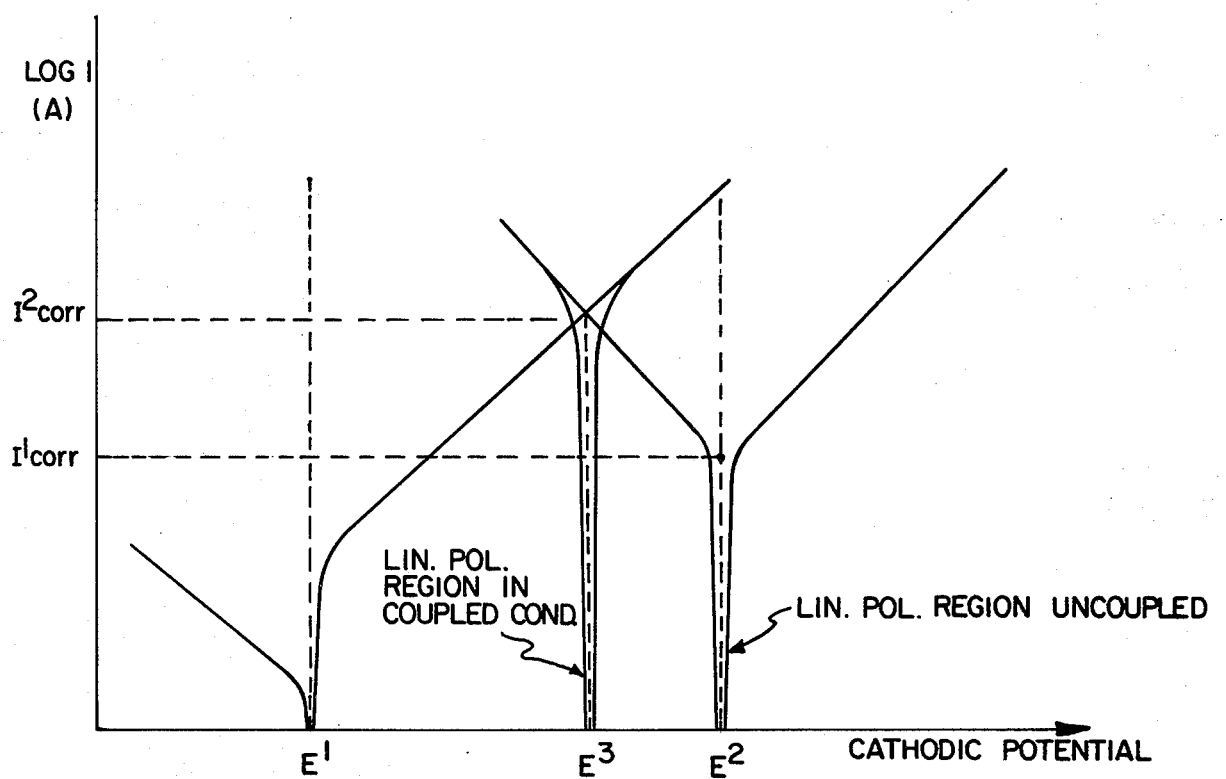
FIG. 1 is a graph depicting the current-potential relationships for galvanic couples.

The theoretical basis for this invention is the mixed potential theory as illustrated in FIG. 1. Here the anodic and cathodic partial current potential characteristics are developed for a noble and a corroding metal when the two are in electrical contact with each other. It is derived that the steady state corrosion potential of the couple is somewhere between $E_1$ and $E_2$ while the corrosion current of the couple attributed to the corrosion of the less noble metal is appropriately higher. The current-potential characteristic of the couple starting at $E_3$ is the one which is measured in the external circuit by regular or linear polarization technique.

Although not necessarily obvious from FIG. 1, it can, nevertheless, be shown theoretically that the current-potential characteristic corresponds to the galvanically accelerated corrosion of the more active metal. A number of comments need to be made with respect to the applicability of this theory.

(a) Note that one needs to consider the total current of both the corroding and the more noble metals rather than their respective current densities.

(b) While the current-potential characteristics for the corroding metal are symmetrical, this is not necessarily true for the more noble metal in the galvanic element since it may or may not corrode. However, it is the cathodic reaction which can occur on the more noble metal of the couple at a much higher rate which is responsible in the galvanic couple. It is this effect which causes the couple to establish a new "corrosion potential" and a new current potential characteristic which is, as indicated above, measured by linear polarization in exactly the same manner as for any other corroding species. In other words, the linear polarization technique does not require the anodic and cathodic reactions to occur on the same metal, a fact which apparently has been overlooked in the past and which, therefore, has precluded the application of the linear polarization technique for galvanic couples.

(c) If a galvanic couple is formed by two corroding metals, then there will be a small contribution to the linear polarization current of the galvanic element from the anodic reaction of the more noble metal. However, since the more noble metal is, in effect, galvanically protected by the less noble metal, this contribution will be very small and can, in general, be neglected.

In summary, it can be said that the advantage of using linear polarization technique for corrosion determination of the corroding metal in a galvanic element consists of the fact that the entire corrosion rate is determined, while with the zero resistance ammeter technique only the galvanic components can be observed.

The linear polarization technique, of course, is subject to the determination of the appropriate Tafel slopes and calibration factors in the same way that this needs to be done for single electrodes. Furthermore, the assessment of galvanic corrosion acceleration is always subject to geometric factors which cannot always be modeled with corrosion probes and may, therefore, be subject to separate studies. However, this latter problem is no different for the linear polarization technique than for the zero resistance ammeter technique.

Figure 2:
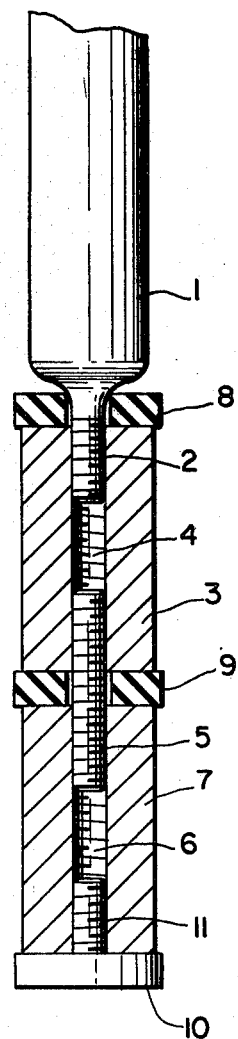
FIGS. 2 and 2A are schematic representations, in section, of galvanically coupled electrodes of this invention.

Referring to FIG. 2, an embodiment of a galvanic electrode of this invention is shown having a holder 1 terminating in a threaded stud 2. A cylindrical rod shaped steel electrode 3 having a central axial threaded bore 4 is mounted on stud 2. A threaded connector member 5, e.g. a steel screw, is threaded into the end of bore 4 opposite the end mounted on stud 2. Connecting member 5 in turn is threaded into a bore 6 of an Inconel electrode 7, identical in dimensions and structure to steel electrode 3. A Teflon washer 8 is positioned between holder 1 and electrode 3 to maintain them in fluid tight relationship. Another Teflon washer 9 is similarly positioned between electrodes 3 and 7 to maintain them in fluid tight relationship. A third Teflon washer 10 is joined to a threaded stud 11 which is threaded into the end of bore 6 opposite the end which receives connecting member 5. Washer 10 provides a fluid tight seal for the outer end of electrode 11.

Figure 2A:
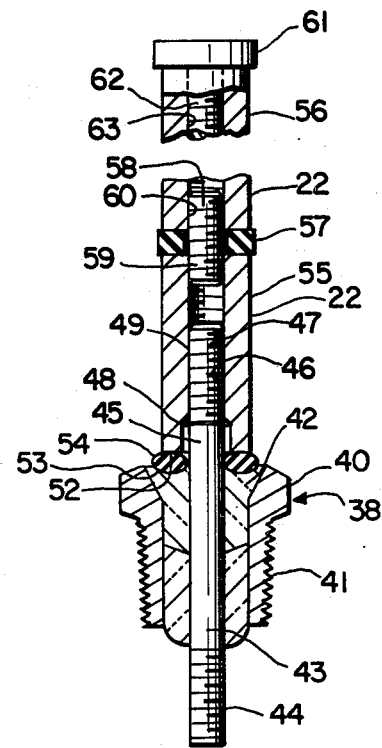
Figure 3:
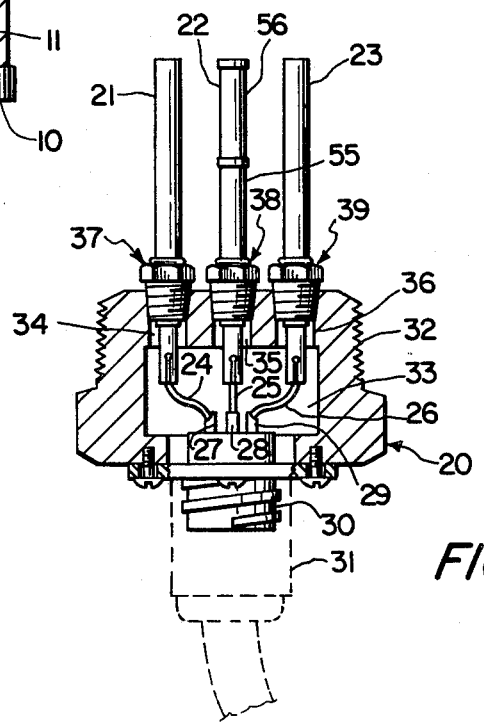
FIG. 3 is a view, partially in section, of a corrosion rate probe utilizing the galvanic electrode of this invention.

FIG. 2A shows a modified version of the galvanic electrode of FIG. 2, adapted to be employed in a probe body of the type shown and claimed in U.S. Pat. No. 3,639,876, issued Feb. 1, 1972 to Homer M. Wilson, the disclosure of which is hereby incorporated by reference. Referring also to FIG. 3, which shows a probe employing the galvanic electrode of FIG. 2A, the probe comprises a metallic body 20, on which are carried replaceable cylindrical electrodes 21, 22 and 23, electrode 22 being a galvanic electrode of this invention and the other two serving as reference and auxiliary electrodes. These electrodes are connected within the body 20 by insulated electrically conductive means 24, 25 and 26, respectively, to the respective terminal lugs, 27, 28 and 29 of a multi-connector electrical fitting 30 carried on top of body 20. Lugs 27, 28 and 29 are electrically common to respective pins, not shown, of fitting 30. Electrical connection to a corrosion rate meter such as disclosed in U.S. Pat. No. 3,406,101, is by a cable connector 31 carrying conductors, not shown, connected respectively to the pins of fitting 30, as shown in U.S. Pat. No. 3,639,876.

Probe body 20 carries external threads 32 which are adapted to engage with interior threads of a pipe fitting, such as shown in U.S. Pat. No. 3,639,876, which forms part of a piping system carrying fluids whose corrosive effect is desired to be determined. A cavity 33, preferably cylindrical, is provided from the top of the body 20 to a region adjacent the lower cylindrical portion carrying the threads 32. The lower portion of the body 20 is provided with a plurality of parallel passageways 34, 35 and 36. These passageways are threaded, at least in part, to receive insulating members 37, 38 and 39, to which the electrodes are secured.

Referring to FIG. 2A as well as FIG. 3, the nature of the insulating member 38, which is identical to insulating members 37 and 39, will be briefly described, a fuller description thereof being contained in U.S. Pat. No. 3,639,876. The insulating member 38 is provided with a metallic sleeve 40 which carries exterior threads 41 to engage with the threads in passageway 35. The sleeve 40 may carry a polygonal external surface readily engageable by pipe tools. A glass element 42 is secured against displacement by compression and a flared shoulder within the sleeve 40. A metallic pin 43 extends centrally of the insulating member 38 in fluid tightness through the glass element 42. Sleeve 40 and pin 43 are sealed in fluid tightness by fusion, which results in glass-to-metal seals. The end of the pin 43 within the cavity 33 is provided with a thread 44 or other attaching surface onto which electrical connection may be made, as by securing electrical conductor 25 thereto. Electrical connections pertaining to the electrodes 21 and 23 through insulating members 37 and 39, respectively are made in identical manner.

Electrode 22 is releasably secured to pin 43, as by a threaded connection, while also providing a fluid tight seal between the electrode and glass element 42. For this purpose the pin 43 is cylindrical with a full diameter portion 45 adjacent the glass element 42, an intermediate threaded portion 46 and a reduced diameter portion 47. Electrode 22 has an axial bore 48 formed into its inner end, such end carrying a seal engaging surface 52. The bore 48 has a reduced diameter threaded portion 49 which engages with the threaded portion 46 of the pin 43. Thus, electrode 22 is threaded upon the pin 43 until a metal-to-metal contact occurs between the abutting surface on the pin 43 and the bore 48. A precise space is left between the presented faces 52 and 53 of electrode 22 and glass element 42, respectively, which space receives an insulating fluid seal 54, e.g., an O ring formed of Viton, into fluid tight engagement. The seal 54 encircles the pin 43 and is compressed within the precise space distance provided to serve effectively as a pressure seal.

As stated above, electrode 22 is a galvanically coupled electrode. In a specific example, it may consist of an inner steel portion 55 and an outer Inconel portion 56 separated by a Teflon washer 57, which provides a fluid tight seal. Electrode portions 55 and 56 are identical in dimensions and structure and are joined in end to end relationship on opposite sides of the washer 57 by a connecting member 58 such as a steel screw threaded into axial bores 59 and 60 of the steel portion 55 and the Inconel portion 56, respectively. Another Teflon washer 61 is joined to a threaded stud 62 which is threaded into axial bore 63 in the outer end of electrode portion 56 to provide a fluid tight seal therefor.

In the above described embodiment, both Viton O rings and Teflon washers may be used interchangeably for the various insulating fluid tight seals shown. The purpose is to prevent seepage of liquid into the threaded portions of the electrode, which, if it occurs, may result in a heightened resistance of the connection between the two parts of the galvanic electrode.

It will be apparent that the configuration of the galvanically coupled electrode is not limited to the one shown in FIGS. 2 and 2A. Any suitable configuration may be employed, including, for example, simple parallel electrodes mounted in an appropriate fashion on a plug. Moreover, it is not necessary that the two parts of the galvanic electrode be dimensionally substantially identical. However, standardization of the results and their interpretation is considerably simplified if they are. Furthermore, the use of the galvanically coupled electrode is not restricted to any particular holder or probe assembly, such as shown in FIG. 3, but can be used in any two or three electrode configuration suitable for use in the linear polarization technique. Moreover, one or more different galvanically coupled electrodes may be employed in a probe holding more than three electrodes, as described and claimed in our copending application, Ser. No. 401,166, filed July 23, 1982, the disclosure of which is hereby incorporated by reference.

The electrodes do not have to be cylindrical; in principle they can have any desired shape. However, both the geometric configuration of the electrodes in relation to each other, as well as their surface areas affect the read-out of the monitoring instrument and are, therefore, part of the calibration. Therefore, the surface areas of the electrodes and the distance between the electrodes in relation to each other must be known ("predetermined") and reproducible. Best results are obtained if the surface area of the electrode exposed to the corrosive environment is most uniform. Thus it is known that the surfaces parallel to the longitudinal axis of the electrode corrode at a rate different from the perpendicular surfaces. This effect is minimized if the electrode is rod-shaped and reasonably long.

EXAMPLE

In order to verify the above theoretical considerations, an experiment was carried out using electrodes of the type shown in FIG. 2. Specifically, galvanic electrodes were constructed, each containing a carbon steel and an Inconel part. These electrodes were used in an autoclave experiment studying the corrosiveness of a chemical cleaning solution containing 20% EDTA at pH 6 in the presence of a corrosion inhibitor.

The corrosion rates on two carbon steel electrodes (AISI-1018 and ASTM-533A) each galvanically coupled to Inconel were monitored by a PAIR Meter parallel to a ASTM-533A uncoupled electrode, employing the technique described in U.S. Pat. No. 3,406,101. The results are shown in FIG. 4 and summarized in Table 1. The corrosion rates were plotted as a function of time as shown in FIG. 4 and the respective areas under the curves averaged by integration. It can be seen from the results listed in Table 1 that the acceleration of the corrosion of the carbon steel due to the galvanic coupling to Inconel is, in fact, observed by both weight loss and PAIR Meter results at exactly the same degree.

TABLE I
CORROSION RATES FOR CARBON STEEL COUPLED AND UNCOUPLED TO INCONEL

| Metal | | Corrosion Rates, MPY[2] | |
|---|---|---|---|
| | | Wt. Loss | PAIR |
| AISI 1018 | Uncoupled | (100)[1] | (100)[1] |
| | Coupled to Inconel | 202 | 192 |
| ASTM 533A | Uncoupled | 61 | 55 |
| | Coupled to Inconel | 155 | 165 |

[1]Results from previous experiments
[2]Mils per year

The technique of this invention measures the total corrosion rate. However, with the use of a single metal electrode and a galvanic electrode containing the same metal, by difference the galvanic acceleration portion may be determined.

It will be evident that various modifications can be made in the apparatus and procedure by those skilled in the art in the light of the above description without departing from the spirit of the invention as defined in the appended claims.

We claim:

1. A probe for use in measuring total corrosion rate comprising a galvanically coupled test electrode comprising two metallic structures, said structures differing from each other in composition, and being mechanically and electrically connected to each other by conductive means and fluid tight sealing means positioned between said structures at the opposite ends of said test electrode, a second rod-shaped electrode serving as a reference electrode, a third rod-shaped electrode serving as an auxiliary electrode, all said electrodes being substantially dimensionally identical; holding means for holding said electrodes parallel to and in proximity with each other and extending outwardly from said holding means; fluid-tight sealing means between each of said electrodes and said holding means; electrical terminal means on said holding means; and conductive means in said holding means for electrically connecting each of said electrodes to a respective terminal in said terminal means.

2. A process for rapidly determining the rate of corrosion of a galvanic couple of two different metals in a corrosive fluid with a galvanically coupled test electrode in the form of two metallic structures, said structures differing from each other in composition, and being mechanically and electrically connected to each other by conductive means, comprising the steps of immersing in the fluid a galvanically coupled test electrode and a second electrode serving as a reference electrode; polarizing the test electrode a small predetermined amount with respect to the reference electrode; and measuring the resultant current, the current being representative of the rate of corrosion of the test electrode.

3. A process for rapidly determining the rate of corrosion of a galvanic couple of two different metals in a corrosive fluid with a galvanically coupled test electrode in the form of two metallic structures, said structures differing from each other in composition, and being mechanically and electrically connected to each other by conductive means, comprising the steps of: immersing in the fluid the galvanically coupled test electrode, a second electrode serving as a reference electrode and a third electrode serving as an auxiliary electrode, all said electrodes being substantially dimensionally identical, having a predetermined exposed surface area and held in fixed proximity to each other; passing a measurable amount of direct current through a circuit including the test electrode, the solution and the auxiliary electrode in an amount sufficient to effect a predetermined measurable polarization of the test electrode with respect to the reference electrode; and measuring the current, the current being representative of the rate of corrosion of the test electrode.

4. The process of claim 3 wherein the current is measured by an instrument calibrated directly in corrosion rates.

5. The process of claim 3 wherein the current is correlated with a corrosion rate polarization resistance ($\Delta E/\Delta I$) curve to determine the corrosion rate.

* * * * *